United States Patent [19]

Decloux et al.

[11] Patent Number: 5,320,328

[45] Date of Patent: Jun. 14, 1994

[54] SUCTION CONTROL VALVE WITH VACUUM BREAKER

[75] Inventors: Henri A. M. Decloux, Herve; Georges P. Katsaros, Liege, both of Belgium

[73] Assignee: Sherwood Medical Company, St. Louis, Mo.

[21] Appl. No.: 105,823

[22] Filed: Aug. 9, 1993

[51] Int. Cl.⁵ ............................................ F16K 3/00
[52] U.S. Cl. ............................ 251/326; 137/625.48; 604/902
[58] Field of Search ............... 251/326, 347; 137/625.48, 625.49, 627.5; 604/33, 119, 902

[56] References Cited

U.S. PATENT DOCUMENTS

| | | | |
|---|---|---|---|
| 3,071,402 | 1/1963 | Lasto et al. | 294/64 |
| 3,645,497 | 2/1972 | Nyboer | 251/148 |
| 3,945,603 | 3/1976 | Fraser | 251/148 |
| 4,430,073 | 2/1984 | Bemis et al. | 604/48 |
| 4,504,266 | 3/1985 | Harle | 604/118 |
| 4,522,592 | 6/1985 | Johnson | 433/95 |
| 4,642,097 | 2/1987 | Siposs | 604/119 |
| 4,671,786 | 6/1987 | Krug | 604/4 |
| 4,725,266 | 2/1988 | Siposs | 604/119 |
| 4,758,224 | 7/1988 | Siposs | 604/119 |
| 4,775,365 | 10/1988 | Swartz | 604/119 |
| 4,787,599 | 11/1988 | Nyboer | 251/148 |
| 4,792,327 | 12/1988 | Swartz | 604/22 |
| 4,813,926 | 3/1989 | Kerwin | 604/118 |
| 4,966,584 | 10/1990 | Nguyen | 604/119 |
| 5,013,300 | 5/1991 | Williams | 604/119 |

FOREIGN PATENT DOCUMENTS 823933 9/1969 Canada .
2365157 9/1976 France .

Primary Examiner—John C. Fox
Attorney, Agent, or Firm—Andrew J. Beck; Montgomery W. Smith; Curtis D. Kinghorn

[57] ABSTRACT

A suction control valve is disclosed that vents to atmosphere the residual vacuum pressure presented to a suction catheter or similar device when the central bore of the valve is completely blocked by a valve member and the device that the suction control valve is controlling becomes occluded. A vent bore extends from the central bore through the valve body underneath the valve member. A vent channel is formed in the underside of the valve member longitudinally aligned with the vent bore and extending a small distance along the underside of the valve body from the end of the valve body. The length of the vent channel is such that when the valve member completely blocks the central bore, the vent channel is positioned over the vent bore thereby forming a vent path from the central bore through the vent bore and vent channel to the atmosphere. Unless the valve body is in the fully closed position, the vent bore is not aligned with the vent channel. As a result, no vent path is formed between the central bore and the atmosphere.

13 Claims, 4 Drawing Sheets

SUCTION CONTROL VALVE WITH VACUUM BREAKER

BACKGROUND OF THE INVENTION

1. Field of the Invention

The invention relates to suction control valves and more particularly to suction control valves that vent to atmosphere residual vacuum pressure in a device to be controlled when the valve is closed.

2. Description of Related Art

Many fields use vacuum pressure or "suction", including the medical field. In the medical field, suction is typically used to remove unwanted material such as saliva or blood from a site through a suction catheter or similar device. A tube attached to a source of suction usually provides suction to the catheter. The tube has a suction control valve that controls the amount of suction provided to the catheter.

U.S. Pat. No. 3,645,497, issued to Robert P. Nyboer on Feb. 29, 1972, shows an example of a suction control valve. The Nyboer device has an elongated valve body with a longitudinal central bore extending between a first and a second end. A movable valve member is transversely and longitudinally mounted within the valve body in an arcuate channel that traverses the central bore. The valve member is made of a deformable material that allows the valve member to move longitudinally into the arcuate channel. The valve member controls the flow of materials through the valve.

As the valve member moves in the channel, the valve member moves from a position that does not obstruct the central bore to a fully closed position that totally obstructs the bore. The valve member controls the amount of suction that passes through the bore by obstructing the bore.

However, when a suction control valve such as the one disclosed in the Nyboer patent is used with a device such as a suction catheter, the ultimate distal end of the suction catheter can contact a patient's tissue. When this occurs, the vacuum pressure within the suction catheter rapidly rises to the vacuum level of the source of the vacuum pressure. This often causes the suction catheter to suck the patient's tissue into the suction catheter. Sucking the patient's tissue into the catheter may damage the tissue.

When the catheter sucks tissue into the catheter and the valve member moves into the fully closed position, a large residual vacuum pressure remains in the suction catheter between the valve member and the patient's tissue. Consequently, the patient's tissue remains drawn into the suction catheter by the residual pressure. Then, if the suction catheter is moved away from the patient's tissue, the tissue may tear. Current suction control devices do not have means for releasing this remaining vacuum pressure from the patient tissue.

Consequently, it is desirable to form a suction control valve that controls vacuum pressure while also allowing the residual vacuum pressure to vent to atmosphere. Such a suction control valve thereby allows the suction catheter to release the patient's tissue without damage to the tissue.

SUMMARY OF THE INVENTION

A suction control valve that vents residual vacuum pressure to vent to atmosphere is disclosed. The present invention modifies a suction control valve, such as the Nyboer device, to vent to atmosphere the residual vacuum pressure formed when the valve member completely occludes the central bore of the valve and the device that the suction control valve is controlling becomes occluded, primarily through contact with a patient's tissue.

In the invention, a vent bore extends from the central bore through the valve body underneath the valve member. The underside of the valve member has a vent channel longitudinally aligned with the vent bore. The vent channel extends a small distance along the underside of the valve body from the end of the valve body. The length of the vent channel is such that when the valve member completely blocks the central bore, the vent channel extends over the vent bore. The vent bore and vent channel form a vent path from the central bore to the atmosphere.

However, when the valve body is not in the fully closed position, there is no alignment of the vent bore with the vent channel. As a result, there is no vent path between the central bore and the atmosphere.

It is therefore an object of the invention to produce a suction control valve that controls vacuum pressure presented through the bore of the valve.

It is another object of the invention to provide a suction control valve that vents vacuum pressure within the central bore to atmosphere when the control valve is in a closed position and the device that the control valve is controlling becomes occluded.

It is another object of the invention to make a suction control valve that is relatively easy to manufacture and simple to use.

These and other objects of the invention will become clear from the description contained herein and with reference to the following detailed description and drawings where like reference numbers refer to like elements.

DETAILED DESCRIPTION OF THE INVENTION

Figure 1:
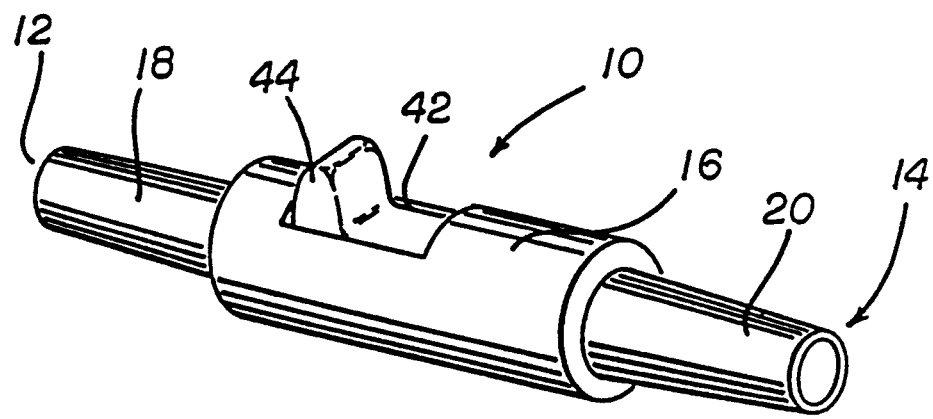
FIG. 1 is a perspective view of the suction control valve of the invention.

FIG. 1 shows the suction control valve of the present invention generally labeled 10. The valve 10 has a distal end 12 and a proximal end 14. The valve preferably has a generally cylindrical body 16 to facilitate manipulation. However, body 16 may have other exterior shapes so long as body 16 has the internal structure described below.

A tapered distal connector 18 extends away from the distal end 12 of body 16 and connects valve 10 to a suction catheter or similar device (not shown). A tapered proximal connector 20 extends away from the proximal end of body 16. Proximal connector 20 connects valve 10 to flexible tubing that is in turn connected to a source of vacuum pressure. Body 16, distal connector 18 and proximal connector 20 are preferably integrally made of a rigid plastic material such as ABS (acrylonitrile butadiene styrene), PP (polypropylene), HDPE (high density polyethylene), PS (polystyrene), PC (polycarbonate), SAN (styrene acrylonitrile), POM (polyacetal), BDS resin, PMMA (polymethyl methacrylate), PA (polyamide), PVC (polyvinyl chloride) or any of the above in combination with fillers. Of these materials, the most preferred material is ABS.

Figure 3:
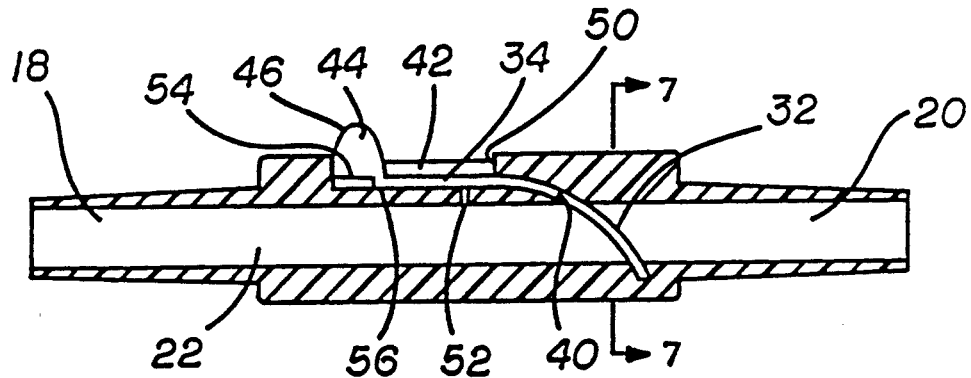
FIG. 3 is a cross-sectional view of the valve shown in FIG. 2 with the valve in an open or non-occluded position.
Figure 7:
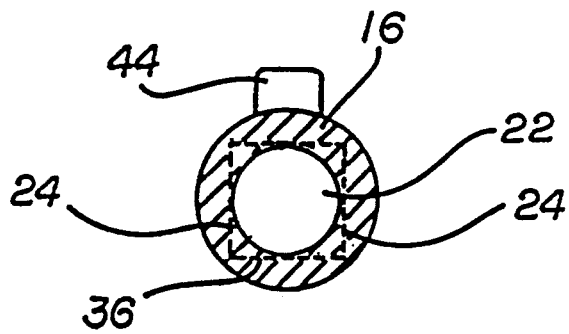
FIG. 7 is a cross-sectional view of the valve shown in FIG. 3 along the cutout labeled 7—7.
Figure 8:
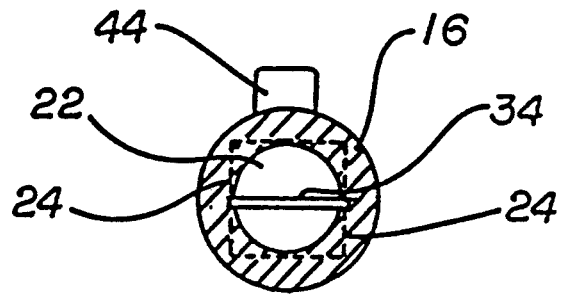
FIG. 8 is a cross-sectional view of the valve shown in FIG. 4 along the cutout labeled 8—8.

Valve 10 has a central bore 22 (FIGS. 3 and 7) that extends from the distal end 12 to the proximal end 14 through body 16 and distal and proximal connectors 18, 20. Central bore 22 is preferably circular in cross-section (FIG. 7).

Body 16 has a pair of elongated internal grooves 24. Grooves 24 run parallel to each other and are located generally on opposite sides of central bore 22. Each groove 24 has an upper and a lower surface 26,28 uniformly spaced apart along the length of each groove 24.

Two sections form each groove 24 in body 16: a distal straight section 30 and a proximal arcuate section 32. Straight section 30 runs parallel to the axis of central bore 22, slightly displaced from the outer edge of central bore 22. Arcuate section 32 extends from the proximal end of straight section 30 and curves transversely across central bore 22.

The opposed edges of grooves 24 are uniformly distant from each other forming an elongated channel of uniform width between grooves 24. The uniform distance of separation of grooves 24 is slightly wider than the diameter of central bore 22. The channel formed between grooves 24 at straight sections 30 extends parallel to the axis of central bore 22. In addition, the channel formed between grooves 24 at straight sections 30 is tangential to and slightly displaced from the outer edge of central bore 22. Between the arcuate sections 32, the channel extends transversely entirely across central bore 22.

An elongated generally rectangular slide 34 spans the channel between grooves 24. Slide 34 is made of a flexible material. The preferred flexible material is a flexible plastic such as LDPE (low density polyethylene), LLDPE (linear low density polyethylene), VLDPE (very low density polyethylene), EVA (ethylene vinyl acetate), EMA (polyethylene methyl acrylate), PP-EPDM (blend of polypropylene and ethylene propylene diene monomer), SEBS (styrene ethylene-butylene styrene) and PU (polyurethane thermoplastic elastomer). Of these materials, the most preferred are LDPE or EVA.

Slide 34 has a thickness about equal to the separation of the upper and lower surfaces 26,28 of grooves 24. This allows grooves 24 to sealingly position slide 34 in the channel formed between grooves 24. In this way slide 34 may slide along grooves 24 constrained by contact between slide 34 and grooves 24 to movement only in the channel formed between grooves 24.

Slide 34 has a length sufficient to extend from the ultimate proximal end 36 of arcuate section 32 entirely across central bore 22. However, when slide 34 contacts the ultimate distal end 38 of straight section 30, the proximal end 40 of slide 34 may or may not extend into the arcuate section 32. If the proximal end 40 of slide 34 does extend into the arcuate section 32, the proximal end 40 of slide 34 should not extend far enough along arcuate section 32 to occlude a portion of central bore 22.

An elongated button recess 42 extends through body 16 from the channel formed between the straight sections 30 to the exterior of body 16. Button recess 42 is elongated in the direction aligned with the axis of central bore 22.

Slide 34 has a button 44 preferably located at the distal end 46 of slide 34. Button 44 extends away from slide 34 through button recess 42 when slide 34 spans grooves 24. Button 44 extends away from slide 34 a sufficient distance to allow a user to contact button 44, with, for example, the user's thumb or finger, from the exterior of body 16. Button recess 42 has a transverse width about equal to the transverse width of button 44. Contact between the side edges of button 44 and button recess 42 constrains button 44 to move in button recess 42 only in a direction parallel to the axis of central bore 22.

Figure 2:
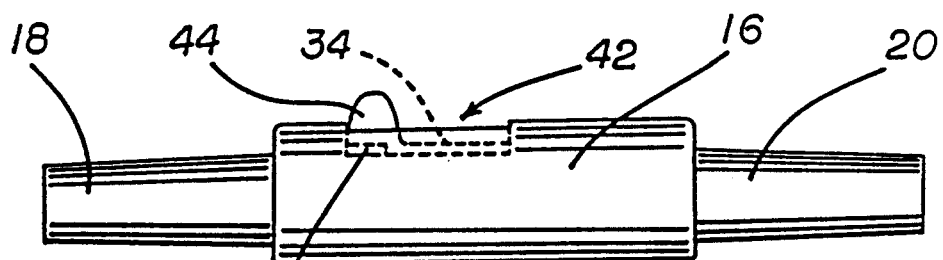
FIG. 2 is a side elevational view of the valve of FIG. 1.
Figure 5:
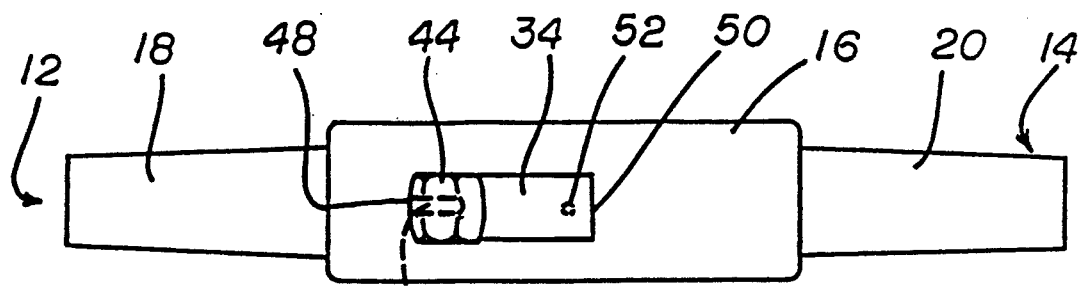
FIG. 5 is a top plan view of the valve of FIG. 1 with the valve member in the open position as shown in FIG. 3.

Movement of button 44 in button recess 42 moves slide 34 along the channel between grooves 24. When button 44 abuts the distal end 48 of button recess 42 (FIG. 5), slide 34 is positioned in the straight section 30 of grooves 24. In this position, no portion of slide 34 extends across central bore 22 (FIGS. 2 and 7).

As button 44 moves proximally in button recess 42, slide 34 moves into the arcuate section 32 of grooves 24 and begins to block central bore 22. Further proximal movement of button 44 moves slide 34 farther and farther along the arcuate section 32. This in turn blocks progressively more of central bore 22. The degree of blockage of central bore 22 determines the amount of vacuum pressure presented to the suction catheter or other device attached to the distal end 12 of the valve 10.

Figure 4:
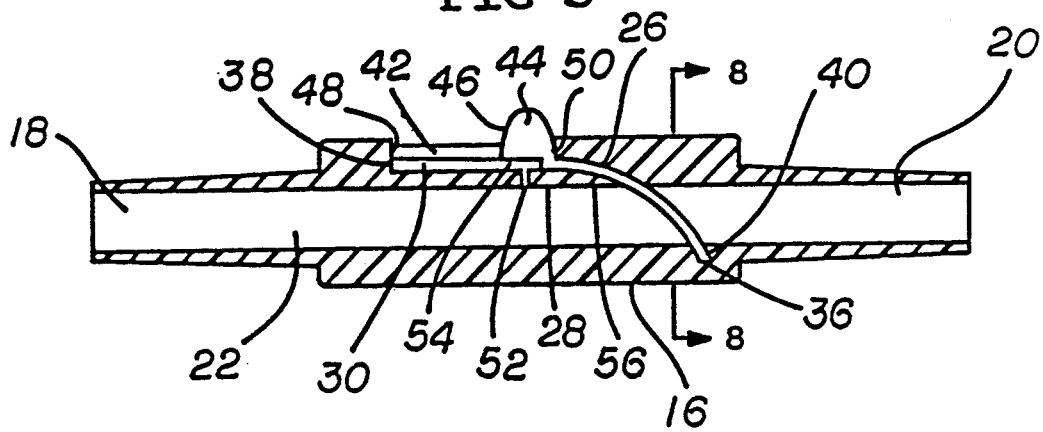
FIG. 4 is a cross-sectional view of the valve of FIG. 2 with the valve member in a closed or occluded position.
Figure 9:
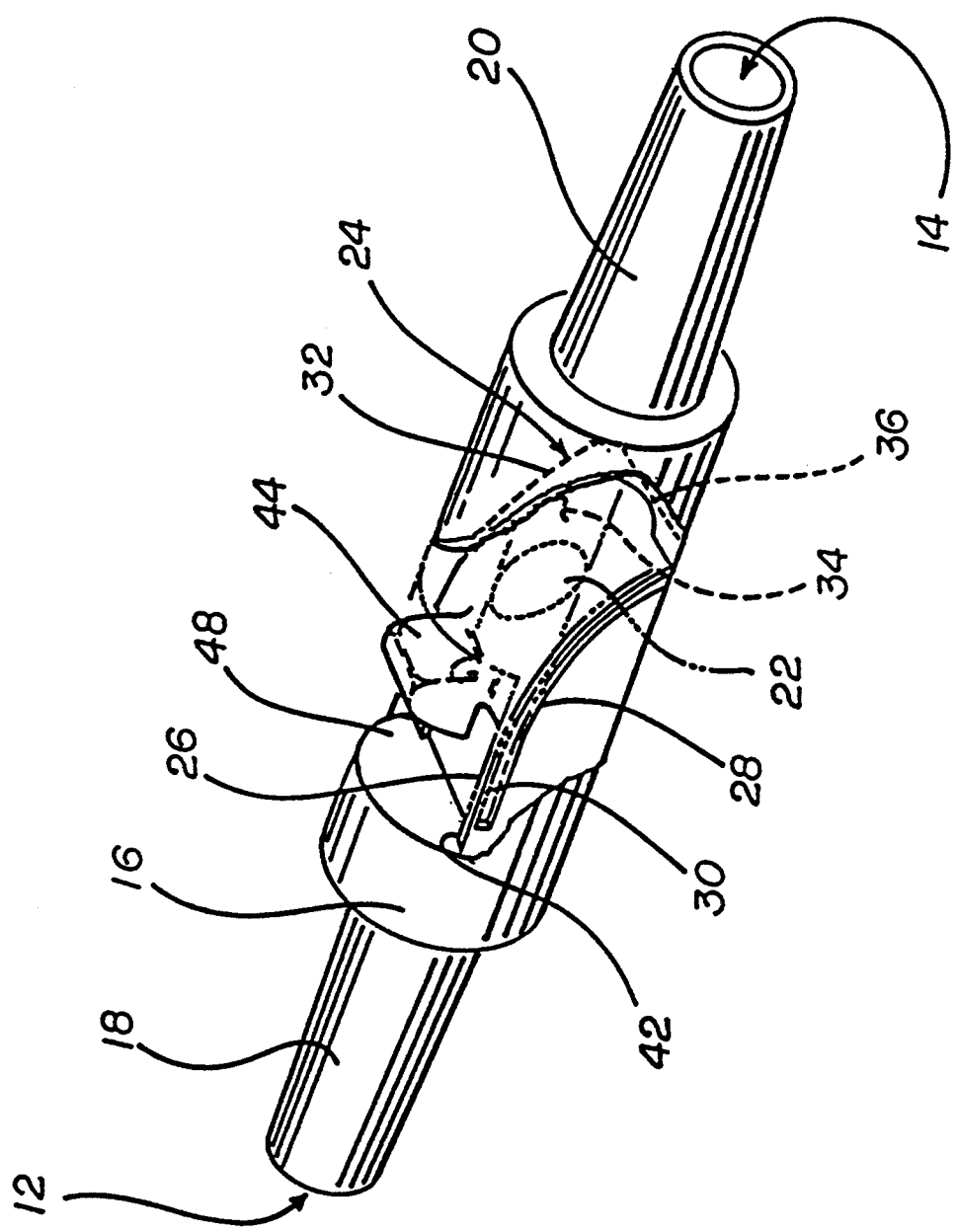
FIG. 9 is a partial cut away of the valve of FIG. 1 showing the occluded position of FIG. 4.

Finally, when button 44 abuts the proximal end 50 of button recess 42 (FIG. 6), slide 34 abuts the ultimate proximal end 36 of the arcuate section 32. In this position, slide 34 entirely blocks central bore 22 (FIGS. 4 and 9). Because slide 34 entirely blocks central bore 22, slide 34 entirely blocks vacuum pressure from the distal end 12 of valve 10.

To use the valve 10, the operator opens valve 10 by moving slide 34 distally in the channel formed between grooves 24. Movement of slide 34 to abut the ultimate distal end 38 of distal straight section 30 presents the maximum vacuum pressure to the ultimate distal end of the suction catheter or similar device. The suction catheter is then placed in contact with fluids and other body components to be removed through the suction catheter by the vacuum pressure. Moving slide 34 proximally along the channel formed between recesses 24 controls the flow volume through the suction catheter.

When the ultimate proximal end of the suction catheter moves into contact with a patient's tissue, the tissue may block the end of the catheter. When this occurs, the vacuum pressure in the catheter rapidly rises to the maximum level of vacuum pressure supplied by the source of vacuum pressure. This can cause the tissue to be sucked into the catheter. Sucking the tissue into the catheter may damage the tissue. However, if the suction catheter is moved away from the patient with the tissue retained by vacuum pressure within the suction catheter, even more damage may be done to the tissue by tearing the tissue away from the patient.

When vacuum pressure sucks the patient's tissue into the catheter as described above and slide 34 moves to entirely occlude central bore 22, high residual vacuum pressure is maintained within the suction catheter. Consequently, the tissue remains sucked in the catheter by the residual vacuum pressure. Removing the ultimate end of the catheter from the patient's tissue releases the residual vacuum pressure but can tear, and thereby damage, the tissue. As long as the source of vacuum pressure presents vacuum pressure to the proximal side of slide 34, opening the valve 10 by moving slide 34 distally along recesses 24 will not decrease the vacuum pressure retained in bore 22.

Figure 11:
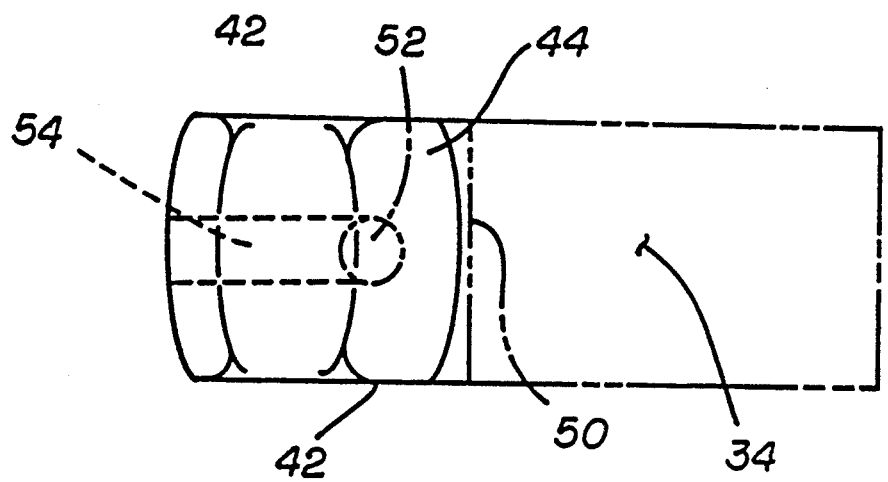
FIG. 11 is an enlarged plan view of the highlighted area of FIG. 6 showing the alignment of the vent bore and vent channel.

To provide vacuum relief to the suction catheter, a vent bore 52 (FIGS. 3 and 4) extends radially from central bore 22 through body 16 to button recess 42. As shown in phantom in FIGS. 6 and 11, vent bore 52 is below the distal end 46 of slide 34 when button 44 abuts the proximal end 50 of button recess 42 and slide 34 entirely blocks central bore 22.

Figure 6:
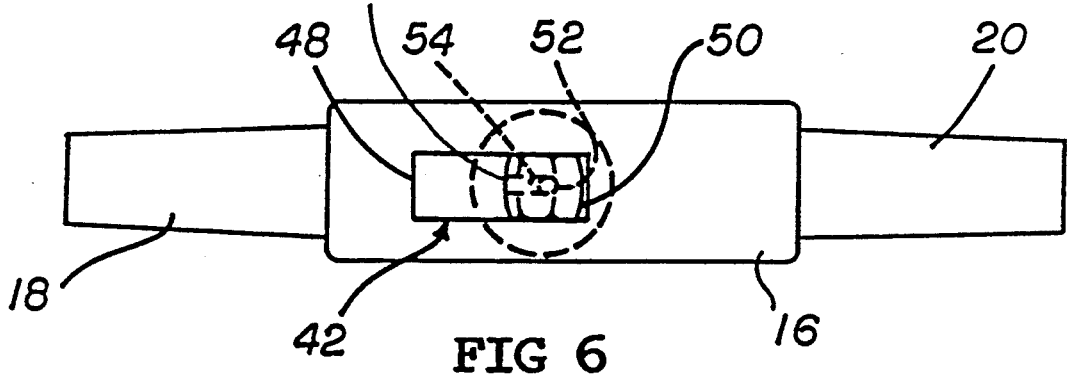
FIG. 6 is a top plan view of the valve of FIG. 1 with the valve member in the closed position as shown in FIG. 4.
Figure 10:
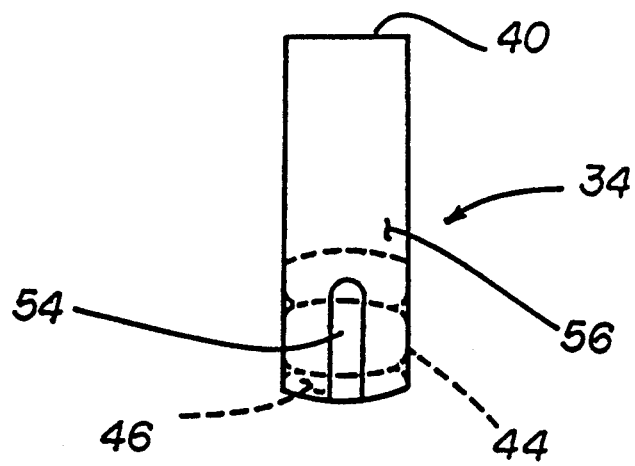
FIG. 10 is a bottom view of the slide of the valve of the invention.

A vent channel 54 (FIGS. 2, 3 and 10) extends into slide 34 along the under side 56 of slide 34. Vent channel 54 extends from the distal end 46 toward the proximal end 40 of slide 34. The distal end of vent bore 54 is open to button recess 42. Vent channel 54 has a length such that vent channel 54 does not extend over vent bore 52 to form an air channel between central bore 22 and the exterior of valve 10 until slide 34 entirely blocks central bore 22 (FIG. 6).

When button 44 abuts the proximal end 50 of button recess 42, vent channel 54 and vent bore 52 are aligned (FIGS. 6 and 11 in phantom) to form an air channel from central bore 22 through vent bore 52, vent channel 54 and button recess 42 to the exterior of the valve 10. As stated above, vent channel 54 does not extend over vent bore 52 to form an air channel between central bore 22 and the exterior of valve 10 until slide 34 entirely blocks central bore 22 (FIG. 4). In any position other than where slide 34 completely blocks central bore 22, contact with the under surface 56 of slide 34 blocks vent bore 52. When slide 34 blocks vent bore 52, no air channel forms between central bore 22 through vent bore 52, vent channel 54 and button recess 42.

Figure 12:
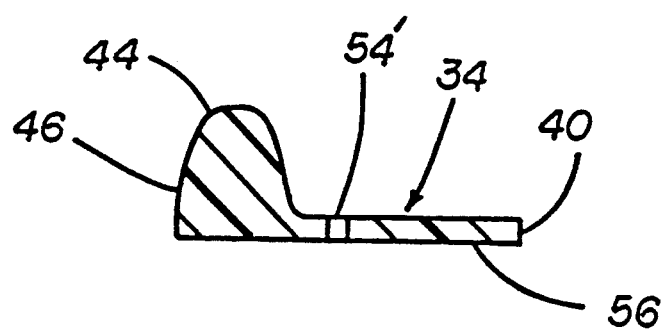
FIG. 12 is a side cross-sectional view of the slide of an alternate embodiment of the invention.

In the preferred embodiment described above, vent channel 54 extends into slide 34 along the under surface 56 of slide 34 from a near at the distal end 46 of slide 34 to the ultimate distal end 46 of slide 34. Alternately, a vent channel 54' may be formed that extends from the under surface 56 of slide 34 through slide 34 to exit on the outer surface 58 of slide 34. The alternate embodiment of vent channel 54' may traverse slide 34 at a right angle to both under surface 56 and outer surface 58 (FIG. 12). Alternately, the vent channel 54' may extend from under surface 56 to outer surface 58 at any angle or along any path so long as an air channel is formed between under and outer surfaces 56, 58.

In any of these alternate configurations of the vent channel 54', vent channel 54, is aligned with vent bore 52 when slide 34 is at its most proximal position abutting the proximal end 36 of arcuate section 32. In all other positions of slide 34, vent channel 54' is not aligned with vent bore 52. As a result, in all positions of slide 34 where vent channel 54' is not aligned with vent bore 52, the under surface 56 of slide 34 covers and blocks vent bore 52 so that no air channel is formed from bore 22 to the exterior of the valve 10 through vent bore 52 and the vent channel.

In any of the embodiments, the configuration of vent bore 52 and vent channel 54 or 54' forms an air channel from central bore 22 that vents the residual vacuum pressure within the suction catheter and central bore 22 distal to slide 34 to the exterior of valve 10 only when slide 34 entirely blocks central bore 22. Because the residual vacuum pressure is vented, vacuum pressure on the patient's tissue is removed so that the suction catheter may be removed from the patient's tissue without tearing or otherwise damaging the tissue.

While the instant invention has been described in connection with a specific embodiment, it is to be understood that the specific details of the description have been given by means of example only and not for limitation. It is clear that changes and modifications may be made to the description contained herein and still be within the scope of the claims. Further, obvious changes and modifications will occur to those skilled in the art.

We claim:

1. A valve device for controlling the vacuum pressure passed through the device comprising:
    a) an elongated rigid valve body having a distal and a proximal end, said body having a central bore extending from said proximal to said distal end of said body, said central bore having a central axis, said body having a pair of opposed parallel grooves defining a channel therebetween, said channel having at least a portion in fluid communicating with the exterior of said body, said grooves separated by a distance at least equal to the diameter of said central bore, said grooves each having a distal end and a proximal end, said grooves each comprising a distal straight section and a contiguous proximal arcuate section, said straight section displaced a distance from the outer edge of said central bore, said arcuate section curving transverse to said central bore so that said channel extends across said central bore between said arcuate sections;
    b) an elongated flexible slide slidably positioned in said channel between said grooves, said slide entirely blocking said central bore when said slide is positioned at said proximal end of said grooves and said slide not blocking said central bore when said slide is positioned at said distal end of said grooves;
    c) means for moving said slide along said channel from a first position where said slide is positioned at said distal end of said grooves to a second position where said slide is positioned at said proximal end of said grooves and along all positions between said first and said second position; and,
    d) means for selectively fluidly communicating said central bore to the exterior of the valve.

2. The valve of claim 1 wherein said means for selectively fluidly communicating includes:
    a) a fluid pathway extending from said central bore to the exterior of said valve;

b) means for blocking said fluid pathway when said slide is not positioned at said proximal end of said grooves.

3. The valve of claim 2 wherein said fluid pathway extends from said central bore to the exterior of said valve entirely distal to said arcuate section of said grooves.

4. The valve of claim 1 wherein said means for selectively fluidly communicating includes:
   a) said body having a vent bore extending from said central bore to said channel; and,
   b) said slide having a vent channel aligned with said vent bore when said slide is moved to said proximal end of said grooves, said vent channel fluidly communicating said vent bore with the exterior of said body, said slide covering and sealing said vent bore except when said slide is moved to a position at said proximal end of said grooves.

5. The valve of claim 1 wherein said straight sections are parallel to the central axis of said central bore.

6. The valve of claim 1 wherein said means for moving said slide along said channel comprises a button extending away from said slide.

7. The valve of claim 6 wherein said body further includes a button recess formed in said body extending from the exterior of said body to at least a portion of said channel and wherein said button extends from said slide through said button recess.

8. A valve device for controlling the vacuum pressure passed through the device comprising:
   a) an elongated rigid valve body having a distal and a proximal end, said body having a central bore extending from said proximal to said distal end of said body, said central bore having a central axis, said body having a pair of opposed parallel grooves defining a channel therebetween, said channel having at least a portion in fluid communicating with the exterior of said body, said grooves separated by a distance at least equal to the diameter of said central bore, said grooves each having a distal end and a proximal end, said grooves each comprising a distal straight section and a contiguous proximal arcuate section, said straight section being parallel to the axis of said central bore and displaced a distance from the outer edge of said central bore, said arcuate section curving transverse to said central bore so that said channel extends across said central bore between said arcuate sections, said body further including a button recess formed in said body extending from the exterior of said body to at least a portion of said channel;
   b) an elongated flexible slide slidably positioned in said channel between said grooves, said slide entirely blocking said central bore when said slide is positioned at said proximal end of said grooves and said slide not blocking said central bore when said slide is positioned at said distal end of said grooves;
   c) means for moving said slide along said channel from a first position where said slide is positioned at said distal end of said grooves to a second position where said slide is positioned at said proximal end of said grooves and along all positions between said first and said second position, said means for moving comprising a button extending away from said slide, said button extending from said slide through said button recess; and,
   d) means for selectively fluidly communicating said central bore distal to said arcuate section of said grooves to the exterior of the valve, said means for selectively fluidly communicating comprising:
      i) a fluid pathway extending from said central bore to the exterior of said valve; and,
      ii) means for blocking said fluid pathway when said slide is not positioned at said proximal end of said grooves.

9. A valve device for controlling the vacuum pressure passed through the device comprising:
   a) an elongated rigid valve body having a distal and a proximal end, said body having a central bore extending from said proximal to said distal end of said body, said central bore having a central axis, said body having a pair of opposed parallel grooves defining a channel therebetween, said channel having at least a portion in fluid communicating with the exterior of said body, said grooves separated by a distance at least equal to the diameter of said central bore, said grooves each having a distal end and a proximal end, said grooves each comprising a distal straight section and a contiguous proximal arcuate section, said straight section being parallel to the axis of said central bore and displaced a distance from the outer edge of said central bore, said arcuate section curving transverse to said central bore so that said channel extends across said central bore between said arcuate sections, said body further including a button recess formed in said body extending from the exterior of said body to at least a portion of said channel;
   b) an elongated flexible slide slidably positioned in said channel between said grooves, said slide entirely blocking said central bore when said slide is positioned at said proximal end of said grooves and said slide not blocking said central bore when said slide is positioned at said distal end of said grooves;
   c) means for moving said slide along said channel from a first position where said slide is positioned at said distal end of said grooves to a second position where said slide is positioned at said proximal end of said grooves and along all positions between said first and said second position, said means for moving comprising a button extending away from said slide, said button extending from said slide through said button recess; and,
   d) means for selectively fluidly communicating said central bore distal to said arcuate section of said grooves to the exterior of the valve, said means for selectively fluidly communicating comprising:
      i) a fluid pathway extending from said central bore to the exterior of said valve, said fluid pathway including:
         A) said body having a vent bore extending from said central bore to said channel; and,
         B) said slide having a vent channel aligned with said vent bore when said slide is moved to said proximal end of said grooves, said vent channel fluidly communicating said vent bore with the exterior of said body, said slide covering and sealing said vent bore except when said slide is moved to a position at said proximal end of said grooves;
      ii) means for blocking said fluid pathway when said slide is not positioned at said proximal end of said grooves.

10. The valve of claim 9 wherein said fluid pathway extends from said central bore to the exterior of said valve entirely distal to said arcuate section of said grooves.

11. The valve of claim 9 further comprising means, attached to said distal end of said body, for fluidly connecting said valve to a source of vacuum pressure.

12. The valve of claim 9 further comprising means, attached to said proximal end of said body, for fluidly connecting said valve to a suction catheter.

13. A valve device for controlling the vacuum pressure passed through the device comprising:
   a) an elongated rigid valve body having a distal and a proximal end, said body having a central bore extending from said proximal to said distal end of said body, said central bore having a central axis, said body having a pair of opposed parallel grooves defining a channel therebetween, said channel having at least a portion in fluid communicating with the exterior of said body, said grooves separated by a distance at least equal to the diameter of said central bore, said grooves each having a distal end and a proximal end, said grooves each comprising a distal straight section and a contiguous proximal arcuate section, said straight section being parallel to the axis of said central bore and displaced a distance from the outer edge of said central bore, said arcuate section curving transverse to said central bore so that said channel extends across said central bore between said arcuate sections, said body further including a button recess formed in said body extending from the exterior of said body to at least a portion of said channel;
   b) an elongated flexible slide slidably positioned in said channel between said grooves, said slide entirely blocking said central bore when said slide is positioned at said proximal end of said grooves and said slide not blocking said central bore when said slide is positioned at said distal end of said grooves;
   c) means for moving said slide along said channel from a first position where said slide is positioned at said distal end of said grooves to a second position where said slide is positioned at said proximal end of said grooves and along all positions between said first and said second position, said means for moving comprising a button extending away from said slide, said button extending from said slide through said button recess; and,
   d) means for selectively fluidly communicating said central bore distal to said arcuate section of said grooves to the exterior of the valve, said means for selectively fluidly communicating comprising:
      i) a fluid pathway extending from said central bore to the exterior of said valve, said fluid pathway including:
         A) said body having a vent bore extending from said central bore to said channel; and,
         B) said slide having a vent channel aligned with said vent bore when said slide is moved to said proximal end of said grooves, said vent channel fluidly communicating said vent bore with the exterior of said body, said slide covering and sealing said vent bore except when said slide is moved to a position at said proximal end of said grooves;
      ii) means for blocking said fluid pathway when said slide is not positioned at said proximal end of said grooves, and
      wherein said fluid pathway extends from said central bore to the exterior of said valve entirely distal to said arcuate section of said grooves;
   e) means, attached to said distal end of said body, for fluidly connecting said valve to a source of vacuum pressure; and,
   f) means, attached to said proximal end of said body, for fluidly connecting said valve to a suction catheter.

* * * * *